(12) United States Patent
Ham et al.

(10) Patent No.: US 10,450,781 B2
(45) Date of Patent: Oct. 22, 2019

(54) ELECTRONIC APPARATUS AND CONTROLLING METHOD THEREOF

(71) Applicant: Samsung Electronics Co., Ltd., Suwon-si, Gyeonggi-do (KR)

(72) Inventors: Jong-gyu Ham, Suwon-si (KR); Young-woong Kim, Gwangmyeong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 15/866,902

(22) Filed: Jan. 10, 2018

(65) Prior Publication Data

US 2018/0209183 A1 Jul. 26, 2018

(30) Foreign Application Priority Data

Jan. 23, 2017 (KR) ........................ 10-2017-0010226

(51) Int. Cl.
| | |
|---|---|
| *B60R 25/00* | (2013.01) |
| *G06F 3/048* | (2013.01) |
| *H04W 12/06* | (2009.01) |
| *H04W 12/04* | (2009.01) |
| *G07C 9/00* | (2006.01) |
| *H04L 29/06* | (2006.01) |
| *E05B 35/00* | (2006.01) |
| *H04W 4/40* | (2018.01) |

(52) U.S. Cl.
CPC .............. *E05B 81/77* (2013.01); *G06F 3/048* (2013.01); *G07C 9/00* (2013.01); *G07C 9/00309* (2013.01); *G07C 9/00817* (2013.01); *H04L 63/083* (2013.01); *H04L 63/0861* (2013.01); *H04W 12/04* (2013.01); *H04W 12/06* (2013.01); *E05B 2035/009* (2013.01); *G07C 9/00563* (2013.01); *G07C 2009/00809* (2013.01); *G07C 2009/00849* (2013.01); *H04W 4/40* (2018.02)

(58) Field of Classification Search
None
See application file for complete search history.

(56) References Cited

U.S. PATENT DOCUMENTS

| | | | |
|---|---|---|---|
| 8,166,523 B2 | 4/2012 | Ezaki et al. | |
| 2010/0237988 A1 | 9/2010 | Hachisuka et al. | |
| 2010/0263031 A1 | 10/2010 | Tsuchiya | |
| 2011/0154485 A1* | 6/2011 | Hyun ................... | H04L 9/3231 726/19 |
| 2015/0317851 A1 | 11/2015 | Linnartz | |

(Continued)

FOREIGN PATENT DOCUMENTS

| | | | |
|---|---|---|---|
| JP | 2002-074365 A | 3/2002 | |
| JP | 2002-312324 A | 10/2002 | |

(Continued)

*Primary Examiner* — Adolf Dsouza
(74) *Attorney, Agent, or Firm* — Jefferson IP Law, LLP

(57) ABSTRACT

An electronic apparatus including a memory configured to store waveform information of a signal received from a user's body, a transceiver configured to receive a signal from an external apparatus using the user's body as a communication medium, and at least one processor configured to confirm whether or not a waveform of the received signal corresponds to the stored waveform information, and perform a predetermined function depending on a confirmation result.

18 Claims, 16 Drawing Sheets

(56) References Cited

U.S. PATENT DOCUMENTS

2016/0013872 A1   1/2016  Astrand et al.
2016/0189451 A1*  6/2016  Yoo ........................ A61B 5/117
                                                              340/5.82
2016/0307380 A1*  10/2016  Ho ..................... G07C 9/00079

FOREIGN PATENT DOCUMENTS

| JP | 2013055574 A | 3/2013 |
|---|---|---|
| KR | 10-2012-0074056 A | 7/2012 |
| KR | 10-1183160 B1 | 9/2012 |
| KR | 10-2016-0077976 A | 7/2016 |

\* cited by examiner

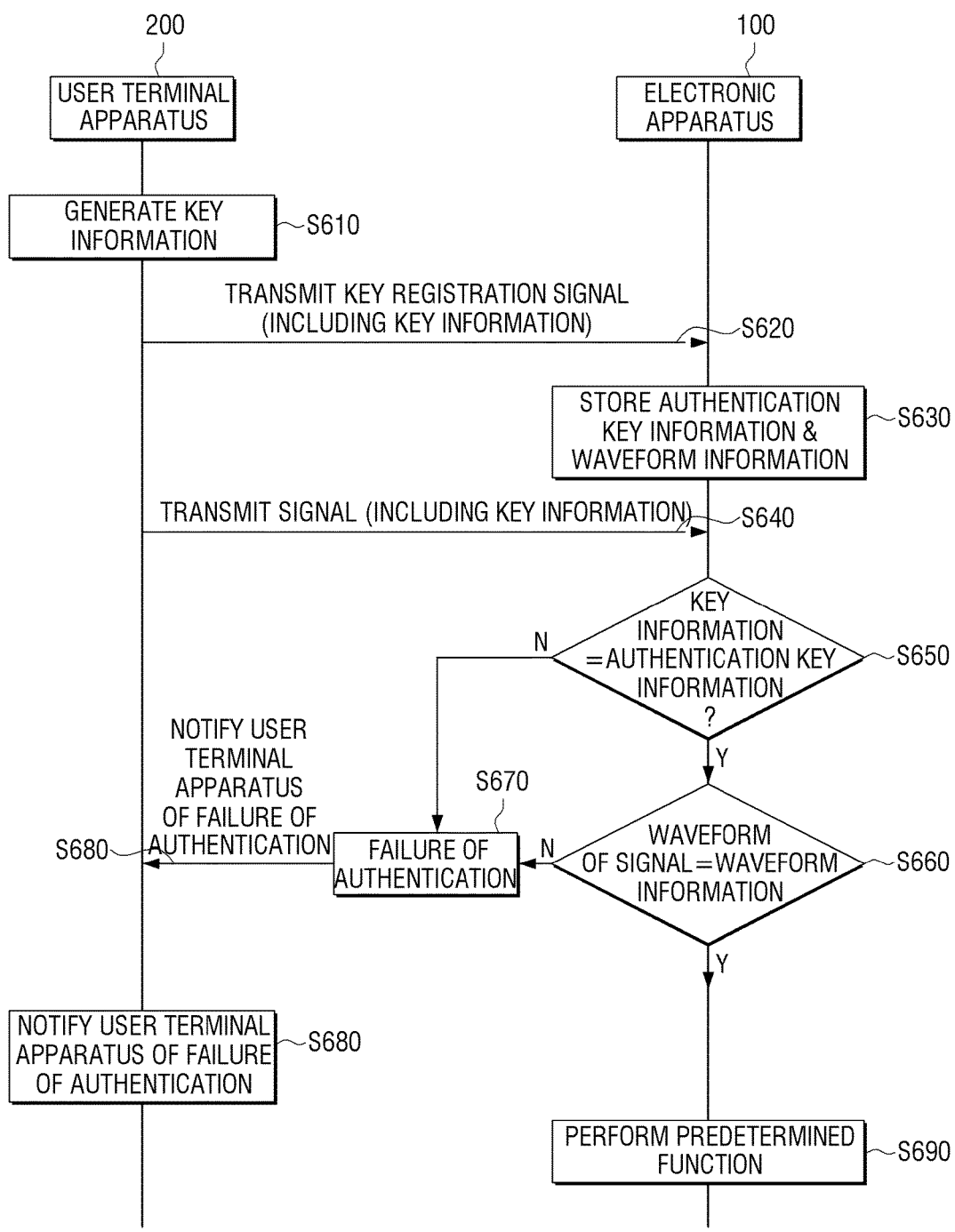

FIG. 9
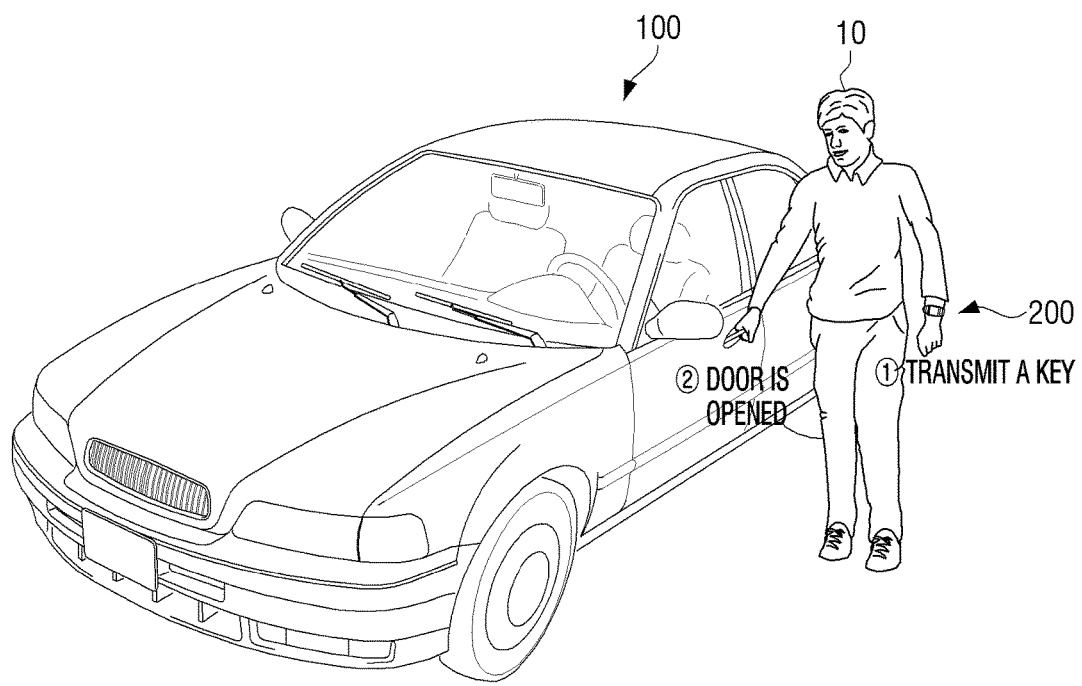
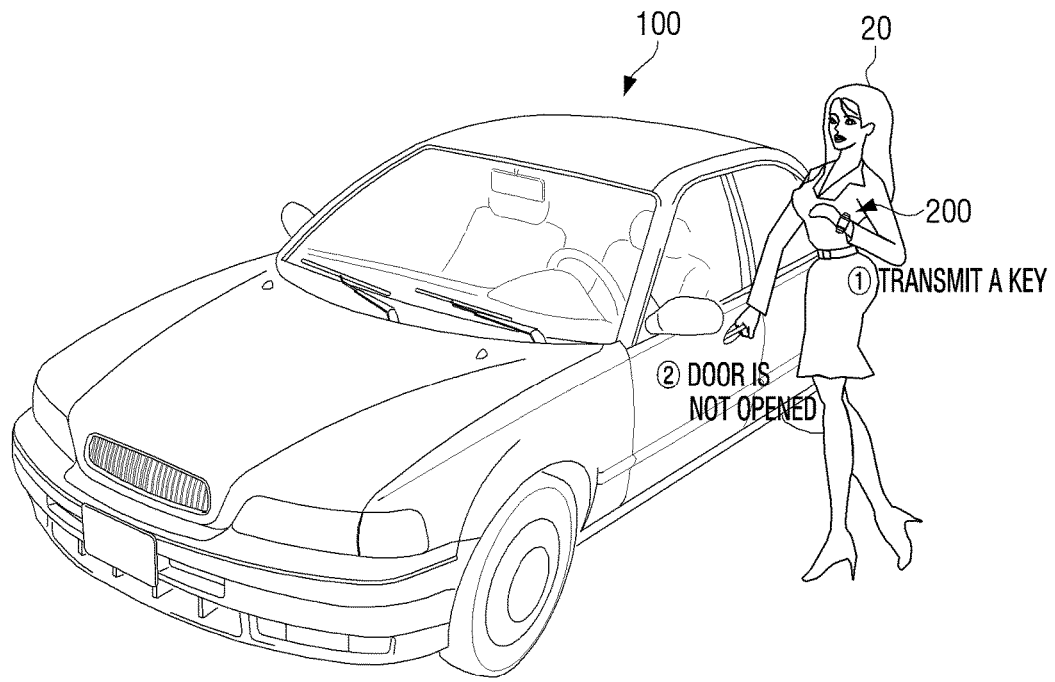

ELECTRONIC APPARATUS AND CONTROLLING METHOD THEREOF

CROSS-REFERENCE TO RELATED APPLICATION(S)

This application claims the benefit under 35 U.S.C. § 119(a) of a Korean patent application filed on Jan. 23, 2017 in the Korean Intellectual Property Office and assigned Serial number 10-2017-0010226, the entire disclosure of which is hereby incorporated by reference.

TECHNICAL FIELD

The present disclosure relates to an electronic apparatus and a controlling method thereof. More particularly, the present disclosure relates to an electronic apparatus capable of performing communication with an external apparatus through a human body, and a controlling method thereof.

BACKGROUND

In accordance with the development of electronic technology, an authentication system performing user authentication using an electronic apparatus has been developed. As an example, a method of authenticating a user by inputting a password specified by the user has been used. As another example, a method of authenticating a user using a personal identification number (PIN) has been used.

As still another example, a method of authenticating a user using physical feature information of the user has been used. For example, an apparatus of opening and closing a door lock by recognizing a fingerprint of a user has been widely used in everyday life. In addition, an authentication system recognizing a pattern of an iris or a pattern of a vein in the back of the hand has also been developed. As another example, a method of authenticating a user using a wearable device has also been used.

However, in the case in which the physical feature information of the user is shared with another apparatus for the purpose of user authentication or is leaked to the outside, there was a risk of leakage of personal information. In addition, in a manner of performing user authentication using the wearable device, when the wearable device is lost, there was a risk that the wearable device will be abused (or misused) by a person acquiring the wearable device.

The above information is presented as background information only to assist with an understanding of the present disclosure. No determination has been made, and no assertion is made, as to whether any of the above might be applicable as prior art with regard to the present disclosure.

SUMMARY

Aspects of the present disclosure are to address at least the above-mentioned problems and/or disadvantages and to provide at least the advantages described below. Accordingly, an aspect of the present disclosure is to provide an electronic apparatus capable of performing communication with an external apparatus through a human body, and a controlling method thereof.

In accordance with an aspect of the present disclosure, an electronic apparatus is provided. The electronic apparatus includes a memory configured to store waveform information of a signal received from a user's body, a transceiver configured to receive a signal from an external apparatus using the user's body as a communication medium, and at least one processor configured to confirm whether or not a waveform of the received signal corresponds to the stored waveform information, and perform a predetermined function depending on a confirmation result.

The memory may store authentication key information corresponding to the predetermined function, and the at least one processor may obtain key information from the received signal and confirm whether or not each of the obtained key information and the waveform of the received signal corresponds to each of the stored authentication key information and the stored waveform information.

The at least one processor may control the transceiver to transmit information for notifying the external apparatus that execution of the predetermined function is impossible to the external apparatus when the obtained key information corresponds to the stored authentication key information and the waveform of the received signal does not correspond to the stored waveform information.

The at least one processor may perform a burglar alarm function when the obtained key information corresponds to the stored authentication key information and the waveform of the received signal does not correspond to the stored waveform information.

The at least one processor may store waveform information generated on the basis of a waveform of a key registration signal in the memory and store key information obtained from the key registration signal as the authentication key information corresponding to the predetermined function in the memory, when the transceiver receives the key registration signal through the user's body.

The electronic apparatus may further include a sensor configured to sense a touch with the user's body, wherein the at least one processor controls the transceiver to transmit a key information request signal through the touched user's body when the touch with the user's body is sensed by the sensor, and obtains the key information from a signal when the signal is received from the touched user's body.

The key information request signal may include at least one of information on a type of the electronic apparatus and unique information of the electronic apparatus.

The processor may generate waveform information on the basis of the waveform of the received signal and update the stored waveform information on the basis of the generated waveform information, when the waveform of the received signal corresponds to the stored waveform information.

The electronic apparatus may be an electronic lock apparatus, and the predetermined function may be a function of releasing a locking state of the electronic lock apparatus.

In accordance with another aspect of the present disclosure, a controlling method of an electronic apparatus is provided. The controlling method includes storing waveform information of a signal received from a user's body, receiving a signal from an external apparatus using the user's body as a communication medium, confirming whether or not a waveform of the received signal corresponds to the stored waveform information, and performing a predetermined function depending on a confirmation result.

The controlling method of an electronic apparatus may further include storing authentication key information corresponding to the predetermined function, wherein the confirming includes obtaining key information from the received signal, and confirming whether or not each of the obtained key information and the waveform of the received signal corresponds to each of the stored authentication key information and the stored waveform information.

The controlling method of an electronic apparatus may further include transmitting information for notifying the external apparatus that execution of the predetermined function is impossible to the external apparatus when the obtained key information corresponds to the stored authentication key information and the waveform of the received signal does not correspond to the stored waveform information.

The controlling method of an electronic apparatus may further include performing a burglar alarm function when the obtained key information corresponds to the stored authentication key information and the waveform of the received signal does not correspond to the stored waveform information.

The controlling method of an electronic apparatus may further include receiving a key registration signal from the external apparatus using the user's body as a communication medium, wherein in the storing of the waveform information, waveform information generated on the basis of a waveform of the received key registration signal is stored, and in the storing of the authentication key information, key information obtained from the received key registration signal is stored as the authentication key information corresponding to the predetermined function.

The controlling method of an electronic apparatus may further include transmitting a key information request signal through the touched user's body when a touch with the user's body is sensed, wherein in the obtaining of the key information, the key information is obtained from a signal when the signal is received through the touched user's body.

The key information request signal may include at least one of information on a type of the electronic apparatus and unique information of the electronic apparatus.

The controlling method of an electronic apparatus may further include generating waveform information on the basis of the waveform of the received signal and updating the stored waveform information on the basis of the generated waveform information, when the waveform of the received signal corresponds to the stored waveform information.

The electronic apparatus may be an electronic lock apparatus, and the predetermined function may be a function of releasing a locking state of the electronic lock apparatus.

In accordance with another aspect of the present disclosure, a non-transitory computer readable recording medium having recorded thereon at least one program comprising commands which, when executed by a computer, performs a method, including: storing waveform information of a signal received from a user's body, receiving a signal from an external apparatus using the user's body as a communication medium, confirming whether or not a waveform of the received signal corresponds to the stored waveform information, and performing a predetermined function depending on a confirmation result.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which:

FIG. 6 is a flow chart for describing operations of a human body communication system according to an embodiment of the present disclosure;

FIG. 9 is a view for describing a user authentication method of an electronic apparatus according to an embodiment of the present disclosure;

Throughout the drawings, it should be noted that like reference numbers are used to depict the same or similar elements, features, and structures.

DETAILED DESCRIPTION

Figure 1:
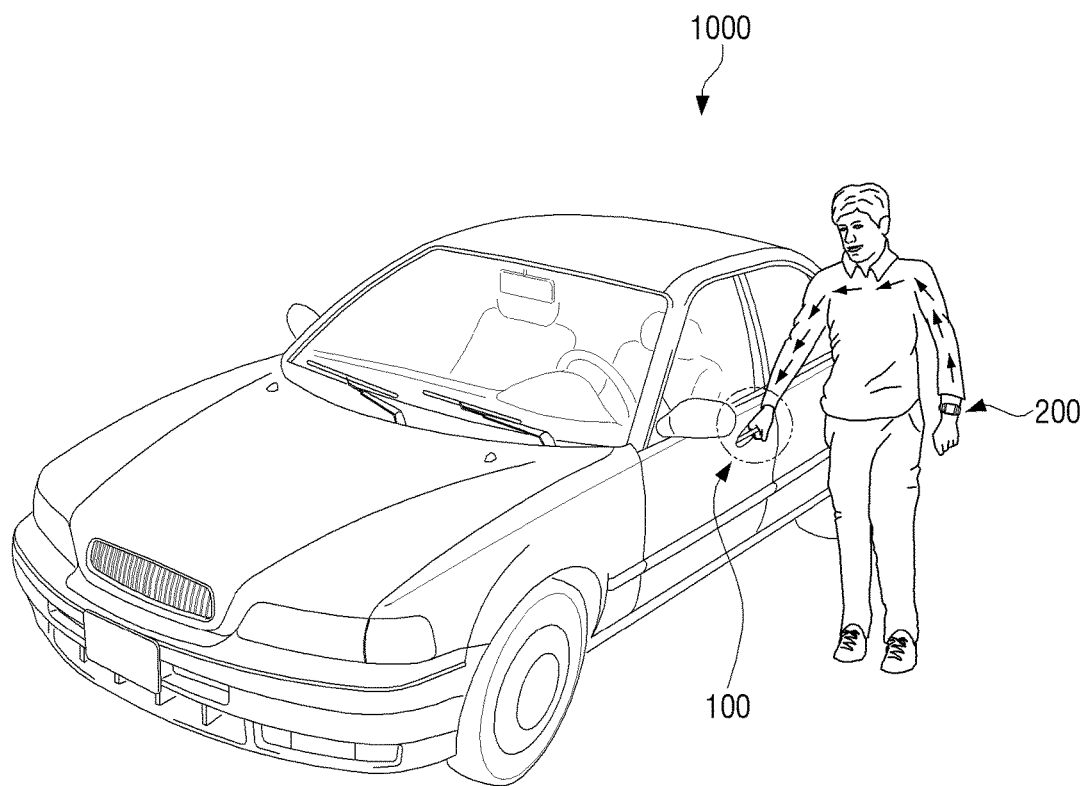
FIGS. 1 and 2 are views for describing a human body communication system according to various embodiments of the present disclosure.

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Terms 'first', 'second', and the like, may be used to describe various components, but the components are not to be construed as being limited by the terms. The terms are used only to distinguish one component from another component.

Terms used in the present disclosure are used only to describe specific various embodiments rather than limiting the scope of the present disclosure. Singular forms are intended to include plural forms unless the context clearly indicates otherwise. It will be further understood that terms "include" or "formed of" used in the present specification specify the presence of features, numerals, steps, operations, components, parts, or combinations thereof mentioned in the present specification, but do not preclude the presence or addition of one or more other features, numerals, steps, operations, components, parts, or combinations thereof.

In various embodiments, a 'module' or a '~er/or' may perform at least one function or operation, and be implemented by hardware or software or be implemented by a combination of hardware and software. In addition, a plurality of 'modules' or a plurality of '~ers/ors' may be integrated in at least one module and be implemented by at least one processor except for a 'module' or an '~er/of' that needs to be implemented by specific hardware.

Hereinafter, various embodiments of the present disclosure will be described in detail with reference to the accompanying drawings so that those skilled in the art to which the present disclosure pertains may easily practice the present disclosure. However, the present disclosure may be modified in various different forms, and is not limited to various embodiments described herein. In addition, in the drawings, portions unrelated to the description will be omitted to obviously describe the present disclosure, and similar reference numerals will be used to describe similar portions throughout the present specification.

Hereinafter, the present disclosure will be described in more detail with reference to the drawings.

FIG. 1 is a view for describing a human body communication system 1000 according to an embodiment of the present disclosure.

Referring to FIG. 1, the human body communication system includes an electronic apparatus 100 and a user terminal apparatus 200.

The electronic apparatus 100 and the user terminal apparatus 200 may perform communication with each other through human body communication.

The human body communication means technology of using a human body as a communication medium such as an electric wire. As terms used as a concept similar to the human body communication (HBC), there are intra-body communication (IBC), body-coupled communication, off-to-on-body communications, body area network (BAN), body sensor networks, body channel, and the like.

As a manner of the human body communication, there are a manner of using a current flowing in a human body, a manner of using an electric field on a surface of the human body, a manner of using vibrations of the human body, and the like.

Each of the user terminal apparatus 200 and the electronic apparatus 100 is provided with an electrode for the human body communication, and when a portion of the human body touches the electrode of the user terminal apparatus 200 and another portion of the human body touches the electrode of the electronic apparatus 100, the user terminal apparatus 200 and the electronic apparatus 100 may transmit and receive signals therebetween.

The user terminal apparatus 200 may transmit a specific signal to the electronic apparatus 100 through the human body communication, and the electronic apparatus 100 may perform a specific function on the basis of the received signal.

The user terminal apparatus 200 may be, for example, a cellular phone, a personal digital assistants (PDA), a tablet personal computer (PC), a smartphone, a wearable device (for example, a wearable device manufactured in a form of a watch, glasses, clothes, a bracelet, a hat, a necklace, or the like), a device that may be attached to a human body (for example, a skin patch device, a device attached to the skin with an electronic tattoo, or the like), a device that may be inserted into the human body (for example, an implantable device, a doseable capsule device, or the like), or the like.

The electronic apparatus 100 may be implemented by various apparatuses, and may be implemented by, for example, an electronic lock apparatus. As an example of a case in which the electronic apparatus is implemented by the electronic lock apparatus, the electronic apparatus 100 may be implemented by a door lock apparatus of a car, as illustrated in FIG. 1. In this case, the electronic apparatus 100 may perform an operation of releasing a locking state of a door of the car on the basis of the signal received from the user terminal apparatus 200 through the human body communication.

Figure 2:
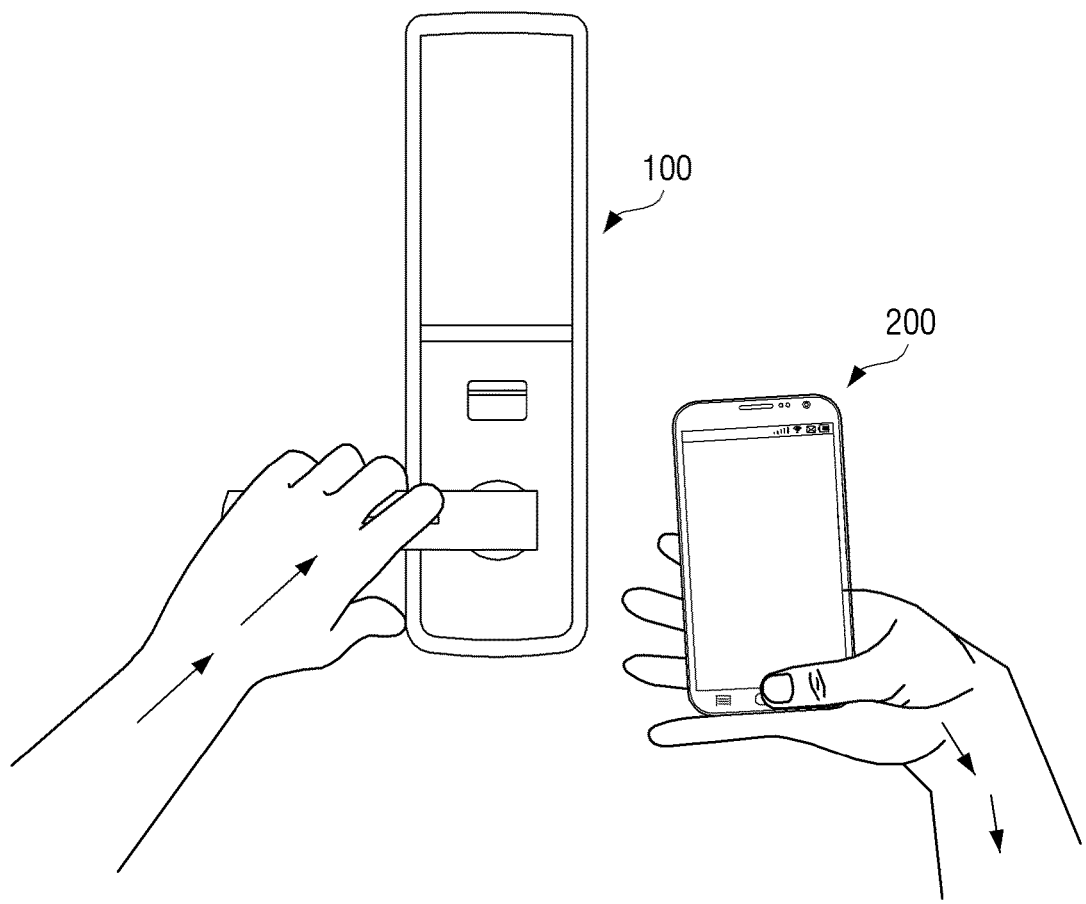

FIG. 2 is a view for describing a human body communication system according to an embodiment of the present disclosure.

Referring to FIG. 2, the electronic apparatus 100 may be implemented by a door lock apparatus. In this case, the electronic apparatus 100 may perform an operation of releasing a locking state of a door on the basis of the signal received from the user terminal apparatus 200 through the human body communication.

As described above, the electronic apparatus 100 may be implemented by the electronic lock apparatus and be embedded in the car, the door, or the like. Alternatively, the electronic apparatus 100 may be manufactured as a separate apparatus from the car, the door, or the like, and be interlocked with the car, a front door, or the like.

Meanwhile, the electronic apparatus 100 may be utilized in any case in which authentication is required, as well as the electronic lock apparatus. For example, the electronic apparatus 100 may be interlocked with a personal device such as a computer, a smartphone, a tablet PC, or the like, and the electronic apparatus 100 may serve to release a locking state (or a security state) of the personal device so that the personal device may be used, on the basis of the signal received from the user terminal apparatus 200.

Hereinafter, the electronic apparatus 100 and the user terminal apparatus 200 described above will be described in more detail.

Figure 3:
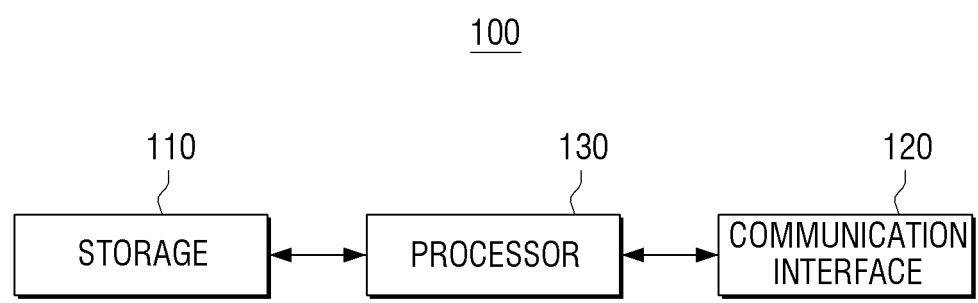
FIG. 3 is a block diagram for describing components of an electronic apparatus according to an embodiment of the present disclosure.

FIG. 3 is a block diagram for describing components of an electronic apparatus 100 according to an embodiment of the present disclosure.

Referring to FIG. 3, the electronic apparatus 100 includes a storage 110 (e.g., a memory), a communication interface 120 (e.g., a transceiver), and a processor 130 (e.g., at least one processor).

Meanwhile, the storage 110 may be implemented by a non-volatile memory, a volatile memory, a flash memory, a hard disc drive (HDD), a solid-state drive (SSD), or the like. The storage 110 is accessed by the processor 130, and readout. Recording, making correction, making deletion, updating, and the like, of data in the storage 110 may be performed by the processor 130. Meanwhile, the storage 110 may be implemented by an external storage medium, for example, a universal serial bus (USB), a web server through a network, or the like, as well as a storage medium in the electronic apparatus 100.

An operating system (O/S) or programs such as various applications and various data such as user set data may be stored in the storage 110, and for example, waveform information of a signal received from a user's body may be stored in the storage 110.

Since various human body configuring materials such as blood, muscle, fat, skin, and the like, configuring the human body are different per human body, characteristics of signals received through the human body are different per human body. For example, a human body tissue in which a content of water is high has a high relative permittivity and conductivity, and a human body tissue in which a content of water is low, such as fat or bone, has a low relative permittivity and conductivity. In addition, noise generated when the signal passes through the fat or the born is smaller than that generated when the signal passes through the muscle. The reason is that resistance of the fat or the born is somewhat higher than that of the muscle. Therefore, even signals have the same data, for example, a waveform of a signal transferred through a user's body having a large amount of fat and a waveform of a signal transferred through a user's body having a small amount of fat are different from each other, and a waveform of a signal transferred through a user's body having a large amount of muscle and a waveform of a signal transferred through a user's body having a small amount of muscle are different from each other.

Therefore, when the signal is received from the human body through the communication interface 120, a waveform of the received signal and waveform information of a signal for a specific user stored in the storage 110 may be compared with each other to confirm whether or not the received signal is received from the specific user.

The electronic apparatus 100 may be used by a plurality of users. In this case, the storage 110 may store waveform information of signals corresponding to each of the plurality of users.

Meanwhile, even though signals are received through the same human body, when transfer paths of the signals are different from each other, waveforms of the signals may also be different from each other. For example, a waveform of the signal that the electronic apparatus 100 receives from the user terminal apparatus 200 through the user's body in the case in which a user wears the user terminal apparatus 200 having a watch form on a left wrist and holds the electronic apparatus 100 with a right hand as illustrated in FIG. 1 may be different from that of the signal that the electronic apparatus 100 receives from the user terminal apparatus 200 through the user's body in the case in which the user wears the user terminal apparatus 200 having the watch form on the left wrist and holds the electronic apparatus 100 with a left hand.

Therefore, a plurality of different waveform information for the same human body may be stored in the storage 110. For example, first waveform information of the plurality of different waveform information corresponds to a signal that the electronic apparatus 100 receives from the user terminal apparatus 200 through the user's body in the case in which the user wears the user terminal apparatus 200 having the watch form on the left wrist and holds the electronic apparatus 100 with the right hand, and second waveform information of the plurality of different waveform information corresponds to a signal that the electronic apparatus 100 receives from the user terminal apparatus 200 through the user's body in the case in which the user wears the user terminal apparatus 200 having the watch form on the left wrist and holds the electronic apparatus 100 with the left hand.

The waveform information of the signal may include at least one of information on an amplitude of the signal, information on a potential of the signal, information on noise included in the signal, information on a distortion level of the signal, and the like. The information on the amplitude of the signal may include information on a magnitude (for example, a current value or a voltage value) of the amplitude of the received signal and/or information on an attenuation constant indicating how much the amplitude of the signal is decreased while the signal moving through the human body. Information on a waveform of an original signal transmitted from the user terminal apparatus 200 may be pre-stored in the storage 110, and a distortion level, an attenuation constant, or the like, of the received signal may be decided by comparing the received signal and the pre-stored information with each other on the basis of the information on the waveform of the original signal.

The waveform information described above may be stored in the storage 110 through a series of processes. This will be described below with reference to FIG. 4.

In addition, authentication key information corresponding to a predetermined function of the electronic apparatus 100 may be stored in the storage 110.

In addition, setting information corresponding to the waveform information may be stored in the storage 110. For example, in the case in which the electronic apparatus 100 is a car, setting information on a driver's seat gradient, a room mirror angle, a rearview mirror angle, and the like, corresponding to the waveform information may be stored in the storage 110.

The processor 130 may generate the waveform information from the waveform of the signal received in a user registering mode, and store the generated waveform information in the storage 110.

The communication interface 120 is a component for performing communication with various external apparatuses. The communication interface 120 may perform communication in various communication manners. As an example, the communication interface 120 may perform communication with an external apparatus in a human body communication manner, which is a manner of transmitting and receiving signals using a human body as a communication medium. In this case, the communication interface 120 includes an electrode touching the human body to receive a signal. The electrode may direct touch the human body or touch the human body with a coating, or the like, interposed therebetween. The communication interface 120 may include a plurality of electrodes. For example, in the case in which the electronic apparatus 100 is implemented by a car, a first electrode of the plurality of electrodes may be disposed on a knob of the car, and a second electrode of the plurality of electrodes may be disposed on a steering wheel of the car.

The communication interface 120 may be connected to the external apparatus through a local area network (LAN) or an Internet network, and may be connected to the external apparatus in a wireless communication manner (for example, Z-wave, internet protocol version 4 (IPv4) over low-power wireless personal area networks (4LoWPAN), 6LoWPAN, radio frequency identification (RFID), long-term evolution device-to-device (LTE D2D), Bluetooth low energy (BLE), general packet radio service (GPRS), Weightless, Edge Zigbee, ANT+, NFC, Infrared Data Association (IrDA_, DECT, wireless local area network (WLAN), Bluetooth (BT), Wireless Fidelity (WiFi), WiFi direct, Global System for Mobile Communications (GSM), Universal Mobile Telecommunications System (UMTS), LTE, WiBRO, or the like). The communication interface 120 may include various communication chips such as a WiFi chip, a Bluetooth chip, a wireless communication chip, and the like.

The processor 130 is a component for controlling a general operation of the electronic apparatus 100. The processor 130 may be implemented by, for example, a central processing unit (CPU), an application specific integrated chip (ASIC), or the like.

When the communication interface 120 of the electronic apparatus 100 receives a key registration signal through the human body, the processor 130 of the electronic apparatus 100 may generate waveform information from a waveform of the received key registration signal and store the generated waveform information in the storage 110.

After the waveform information is stored as described above, when the communication interface 120 receives a signal through the human body, the processor 130 confirms whether or not a waveform of the received signal corresponds to the waveform information stored in the storage 110, and performs a predetermined function depending on a confirmation result.

A process of storing the waveform information in the storage 110 will be described with reference to FIGS. 4A and 4B.

Figure 4A:
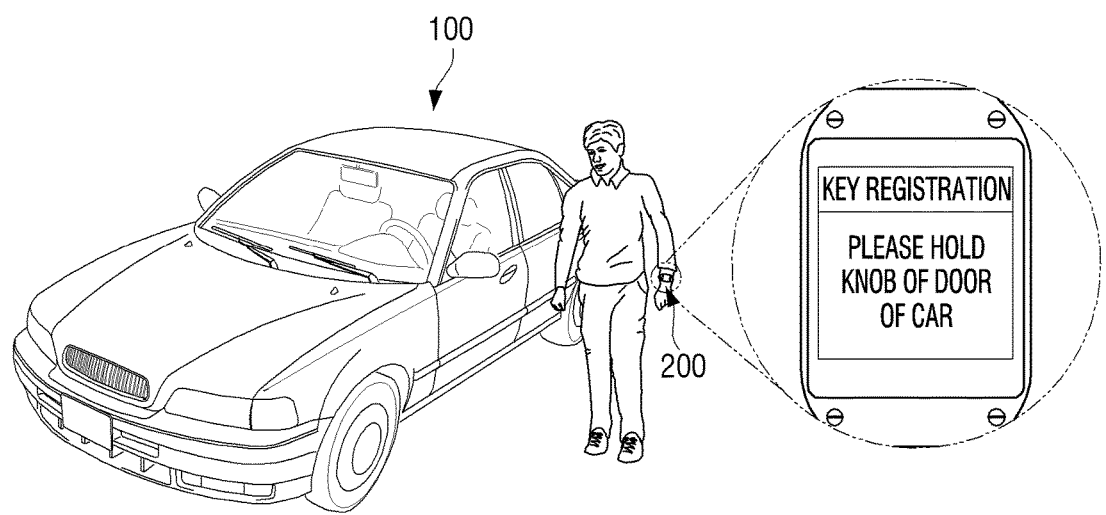
FIGS. 4A, 4B, and 5 are views for describing a key registering process according to various embodiments of the present disclosure.
Figure 4B:
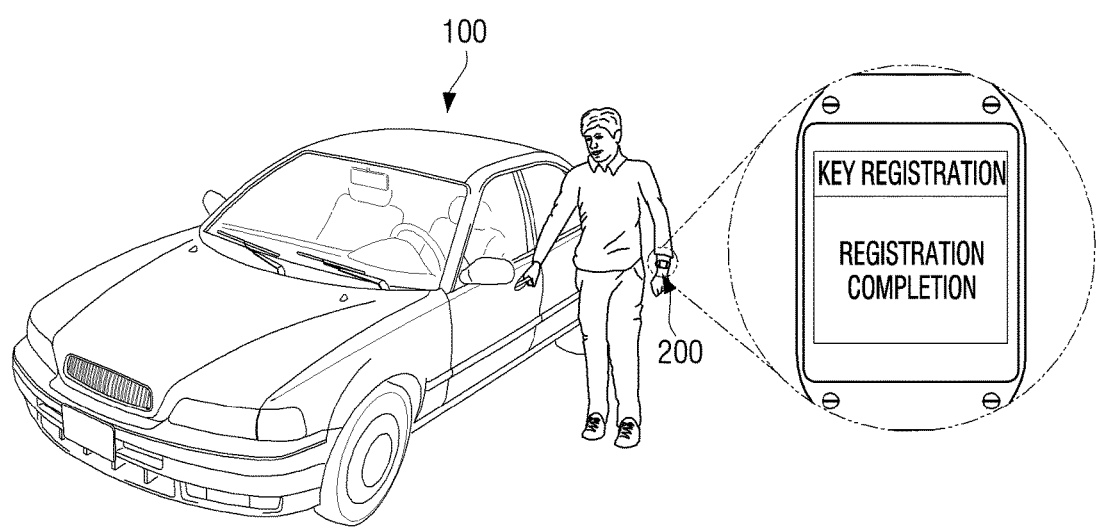

FIGS. 4A and 4B are views for describing a waveform information storing process according to various embodiments of the present disclosure.

Referring to FIG. 4A, the user terminal apparatus 200 worn on a use's wrist may enter a key registration signal transmittable state depending on a predetermined user manipulation. For example, the user terminal apparatus 200 may store an application for interlocking with the electronic apparatus 100, provide a menu for transmission of a key registration signal when the application is executed, and enter the key registration signal transmittable state when the user selects the menu. For example, the application may be downloaded by other electronic apparatuses interlocked with the user terminal apparatus 200 and be installed in the user terminal apparatus 200.

In addition, in the key registration signal transmittable state, the user terminal apparatus 200 may display, for example, a screen for inducing a user to touch the electronic apparatus 100. In the case in which the electronic apparatus 100 is an electronic door lock apparatus of the car, a phrase "please hold a knob of a door of a car" may be displayed on the user terminal apparatus 200, as illustrated in FIG. 4A.

When the user holds the electronic apparatus 100 in the key registration signal transmittable state, the user terminal apparatus 200 may transmit the key registration signal to the electronic apparatus 100 through a user's body.

When the communication interface 120 receives the key registration signal through the user's body, the processor 130 of the electronic apparatus 100 may generate waveform information on the basis of a waveform of the received key registration signal, and store the generated waveform information in the storage 110.

In this case, the processor 130 may store the waveform information generated form the received key registration signal in the storage 110 only when a predetermined condition is satisfied. As an example, in the case in which the electronic apparatus 100 is the electronic lock apparatus, when the key registration signal is received in a state in which a locking state of the electronic apparatus 100 is released, the processor 130 may decide that the predetermined condition is satisfied. As another example, in the case in which it is confirmed that predefined data are included in the received key registration signal, the processor 130 may decide that the predetermined condition is satisfied. Here, it is preferable that the predefined data correspond to information that may be recognized by only a user having authority to use the electronic apparatus 100. For example, the predefined data may be data provided to a purchaser at the time of purchasing the car. Alternatively, the predefined data may be authentication data provided form an external server. In detail, the user terminal apparatus 200 and the electronic apparatus 100 may be connected to the external server, the external server may receive user information, or the like, input from the user terminal apparatus 200 and transmit the authentication data to the user terminal apparatus 200 when it is confirmed that a user is a valid user of the car, the user terminal apparatus 200 may transmit the key registration signal including the authentication data to the electronic apparatus 100, and the electronic apparatus 100 may request the external server to confirm whether or not the received authentication data is provided to the valid user and decide that the predetermined condition is satisfied when the confirmation is conducted.

When the waveform information generated on the basis of the key registration signal transmitted from the user terminal apparatus 200 is stored in the electronic apparatus 100, for example, the electronic apparatus 100 may transmit a storing completion signal to the user terminal apparatus 200 through the user's body, and the user terminal apparatus 200 receiving the storing completion signal may display a screen for notifying the user of registration completion, as illustrated in FIG. 4B. Meanwhile, the electronic apparatus 100 may also transmit the storing completion signal to the user terminal apparatus 200 in another communication manner such as Bluetooth, or the like, instead of transmitting the storing completion signal through the user's body.

The waveform information stored as described above is later compared with a waveform of a signal that the electronic apparatus 100 receives from the user terminal apparatus 200 through the user's body. The electronic apparatus 100 may perform a predetermined function depending on a comparison result.

Figure 5:
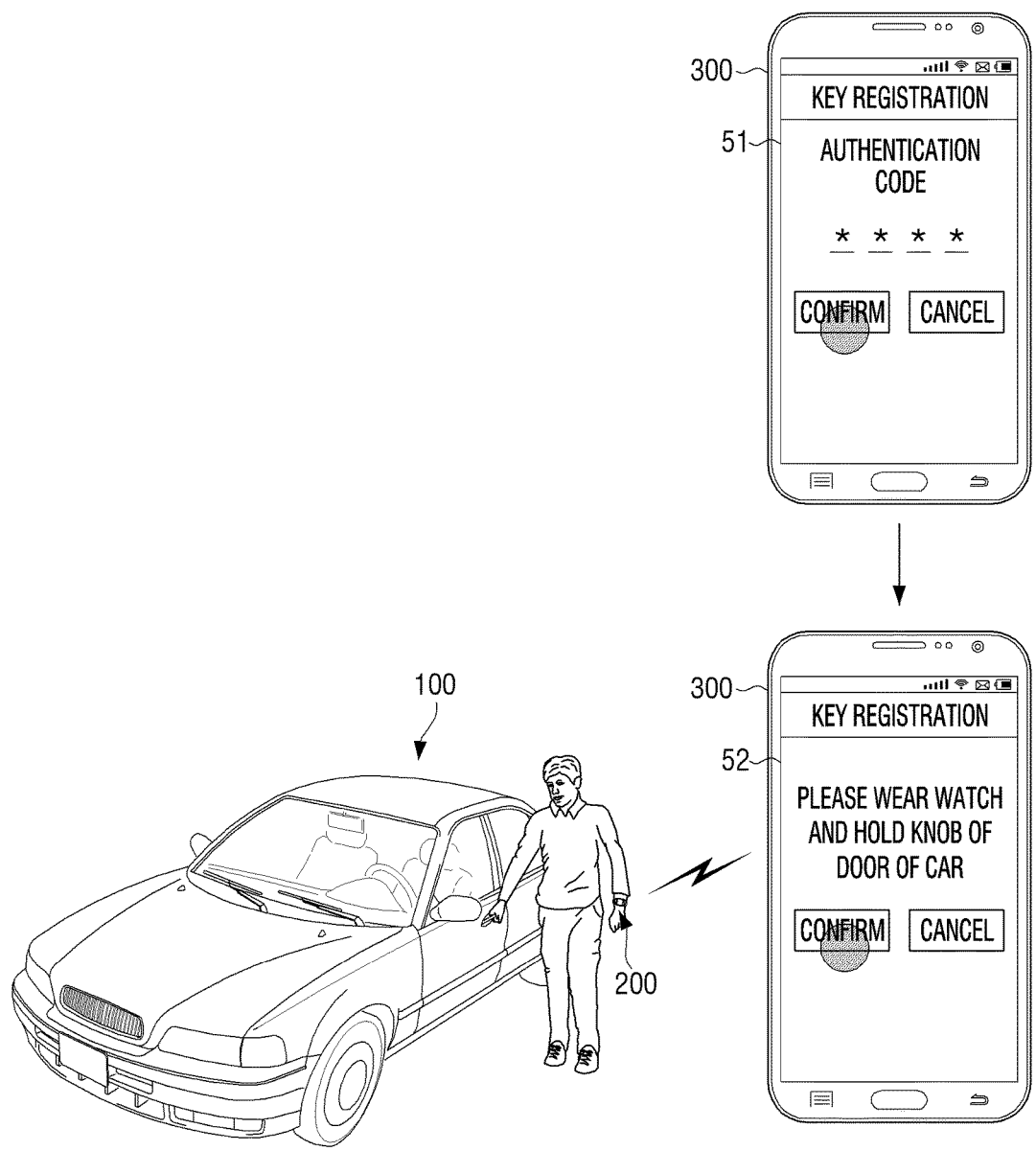

FIG. 5 is a view for describing a waveform information storing process according to an embodiment of the present disclosure.

Referring to FIG. 5, the user terminal apparatus 200 may transmit a key registration signal to the electronic apparatus 100 under a control of an external apparatus 300. The external apparatus 300, which is an apparatus capable of performing communication with the user terminal apparatus 200, may be implemented by, for example, a smartphone, a tablet PC, a computer, or the like. The external apparatus 300 and the user terminal apparatus 200 may communicate with each other in various wireless communication manners such as Bluetooth, WiFi, and the like. FIG. 5 illustrates a case in which the external apparatus 300 is implemented by the smartphone.

An application for interlocking with the user terminal apparatus 200 may be stored in the external apparatus 300, and when the application is executed and a specific user manipulation is input, the external apparatus 300 may display a user interface (UI) screen 51 for receiving a predefined authentication code in order to transmit the key registration signal. It is preferable that the predefined authentication code corresponds to information that may be recognized by only a user having authority to use the electronic apparatus 100. For example, the predefined authentication code may be a code provided to a purchaser at the time of purchasing the car. Alternatively, the predefined authentication code may be provided from an external server. In detail, the external apparatus 300 may receive input user information, and transmit the input user information to the external server. The external server provides the authentication code to the external apparatus 300 when it is decided that the received user information corresponds to a valid user of the electronic apparatus 100. The user may input the provided authentication code to the UI screen 51.

Meanwhile, although a case in which the input of the authentication code is required is described above, this process may also be omitted.

When the authentication code is input, the external apparatus 300 may display a guide UI 52. The guide UI 52 may be a UI for notifying the user of an action that needs to be taken by the user for the purpose of human body communication. When a confirmation button is selected on the guide UI 52, the external apparatus 300 may transmit a control signal for commanding the user terminal apparatus 200 to transmit the key registration signal to the electronic apparatus 100 through the human body communication to the user terminal apparatus 200.

In this case, the external apparatus 300 may provide the key registration signal together with the control command to the user terminal apparatus 200, and the user terminal apparatus 200 may transmit the key registration signal provided from the external apparatus 300 to the electronic apparatus 100. Alternatively, when the external apparatus 300 transmits the control command, the user terminal apparatus 200 may transmit the key registration signal to the electronic apparatus 100 on the basis of information pre-stored in the user terminal apparatus 200.

When the key registration signal is received through the human body communication, the processor 130 of the electronic apparatus 100 may generate waveform information on the basis of a waveform of the received key registration signal, and store the generated waveform information in the storage 110.

In this case, the processor 130 may store the waveform information generated form the received key registration signal in the storage 110 only when a predetermined condition is satisfied. As an example, the authentication code input to the UI screen 51 for receiving the authentication code may be included in the key registration signal, and the processor 130 may decide that the predetermined condition is satisfied when the authentication code included in the key registration signal and a pre-stored authentication code coincide with each other. As another example, in the case in which the authentication code input to the UI screen 51 for receiving the authentication code is an authentication code provided by the external server, the electronic apparatus 100 may decide that the predetermined condition is satisfied when it is confirmed that the authentication code included in the key registration signal is the authentication code provided by the external server. As still another example, when the key registration signal is received in a state in which a locking state of the electronic apparatus 100 is released, the processor 130 may decide that the predetermined condition is satisfied.

When the waveform information generated on the basis of the key registration signal transmitted from the user terminal apparatus 200 is stored in the electronic apparatus 100, for example, the electronic apparatus 100 may transmit a storing completion signal to the user terminal apparatus 200 through the user's body, and the user terminal apparatus 200 receiving the storing completion signal may notify the external apparatus 300 of storing completion in a wireless communication manner such as Bluetooth, or the like. The external apparatus 300 notified of the storing completion may display a screen for notifying the user of registration completion. Alternatively, the electronic apparatus 100 may directly communicate with the external apparatus 300 to directly transmit the storing completion signal to the external apparatus 300 through Bluetooth communication, or the like.

The waveform information stored as described above is later compared with a waveform of a signal that the electronic apparatus 100 receives from the user terminal apparatus 200 through the user's body. The electronic apparatus 100 may perform a predetermined function depending on a comparison result.

As an example, the processor 130 may perform the predetermined function when it is confirmed that the stored waveform information and the waveform of the received signal coincide with each other.

Meanwhile, according to another example, the processor 130 may perform the predetermined function only when it is confirmed that the waveform of the received signal coincides with the stored waveform information and key information obtained from the received signal coincides with pre-stored authentication key information. That is, the electronic apparatus 100 may be subjected to a double authentication process.

In detail, the storage 110 may store the waveform information and the authentication key information corresponding to the predetermined function, and the processor 130 may obtain the key information from the received signal and confirm whether or not the obtained key information corresponds to the authentication key information pre-stored in the storage 110 and whether or not the waveform of the received signal corresponds to the waveform information pre-stored in the storage 110.

In addition, the processor 130 may perform the predetermined function when the key information obtained from the signal coincides with the pre-stored authentication key information and the waveform of the signal coincides with the pre-stored waveform information as a confirmation result.

The authentication key information may be included in the key registration signal and be transmitted from the user terminal apparatus 200 to the electronic apparatus 100 through the human body communication, and the processor 130 may obtain the key information from the received signal and store the obtained key information as the authentication key information corresponding to the predetermined function in the storage 110, and may generate the waveform information on the basis of the waveform of the received signal and store the generated waveform information in the storage 110.

The key information included in the key registration signal and transmitted to the electronic apparatus by the user terminal apparatus 200 may be generated on the basis of biometric information collected by the user terminal apparatus 200.

The user terminal apparatus 200 can collect physical feature information related to, for example, a user's face, iris, electrocardiogram (ECG), fingerprint, vein, touch pattern, gait, and the like, and generate the key information on the basis of the collected physical feature information.

For example, the user terminal apparatus 200 may include an infrared camera, and photograph heat emitted from a blood vessel of a user's face by the infrared camera to collect the physical feature information. Alternatively, the user terminal apparatus 200 may include a fingerprint recognizing sensor obtaining a fingerprint image by a visible ray, an ultrasonic wave, or electricity, and collect the physical feature information by the fingerprint recognizing sensor. Alternatively, the user terminal apparatus 200 may include a camera for photographing a use's eye, and create a coordinate for a boundary between a pupil and an iris of the photographed user's eye and then generate data on the coordinate to collect the physical feature information. Alternatively, the user terminal apparatus 200 may include an electrode for measuring ECG, and collect the ECG as the physical feature information. Alternatively, the user terminal apparatus 200 may include a charge coupled device (CCD) camera, and photograph a vein distribution using a principle that red cells absorb an infrared ray to collect the physical feature information. Alternatively, the user terminal apparatus 200 may include a touch screen, and analyze a user's touch pattern on the touch screen to collect the physical feature information. Alternatively, the user terminal apparatus may include a motion sensor such as a gyro sensor, an acceleration sensor, or the like, and analyze a user's gait pattern to collect the physical feature information. However, these are only examples, and the user terminal apparatus 200 may collect the physical feature information by various kinds of technology.

Since the key information generated on the basis of the collected physical feature information is unique to the user, security for the electronic apparatus 100 may be enhanced. In addition, in an embodiment of the present disclosure, the waveform of the signal received through the human body as well as the key information are considered, and the security may thus be further enhanced. An embodiment in which both of the key information and the waveform information are considered will be described in more detail with reference to a flow chart of FIG. 6.

FIG. 6 is a flow chart for describing operations of a user terminal apparatus 200 and an electronic apparatus 100 according to an embodiment of the present disclosure.

First, the user terminal apparatus 200 generates the key information at operation S610. The user terminal apparatus 200 can collect the physical feature information such as a user's face, iris, ECG, fingerprint, vein, touch pattern, gait pattern, and the like, and generate the key information on the basis of the collected physical feature information. When the key information is generated and used instead of using physical information itself of the user, a risk that the physical information of the user will be leaked to the outside may be decreased.

In addition, the user terminal apparatus 200 transmits the key registration signal including the generated key information to the electronic apparatus 100 through the human body communication at operation S620. The key registration signal may further include the user information. A key registration signal transmission command may be input by, for example, a user manipulation conducted in the user terminal apparatus 200 or a user manipulation conducted in the external apparatus or the electronic apparatus 100.

The electronic apparatus 100 obtains the key information from the key registration signal received through the human body communication, generates the waveform information on the basis of the waveform of the key registration signal, stores the obtained key information as the authentication key information related to the predetermined function in the storage 110, and stores the generated waveform information in the storage 110 at operation S630. The key registration signal may include the user information, and the electronic apparatus 100 may store and manage the authentication key information and the waveform information in the storage 110 for each user on the basis of the user information included in the key registration signal.

Then, the user terminal apparatus 200 transmits a signal including the key information for the purpose of execution of the predetermined function of the electronic apparatus 100 through the human body communication at operation S640. According to an embodiment of the present disclosure, the signal may be automatically transmitted even if the user holds the electronic apparatus 100.

As an example, the electronic apparatus 100 may trigger the transmission of the signal. For example, the electronic apparatus 100 may include a sensor (for example, a touch sensor, or the like) sensing a touch of the human body, and transmit a key information request signal to the user terminal apparatus 200 through the touched human body when the touch of the human body is sensed by the sensor. The user terminal apparatus 200 receiving the key information request signal may transmit the signal including the key information to the electronic apparatus 100. The present embodiment will be described in more detail with reference to FIG. 7A.

Figure 7A:
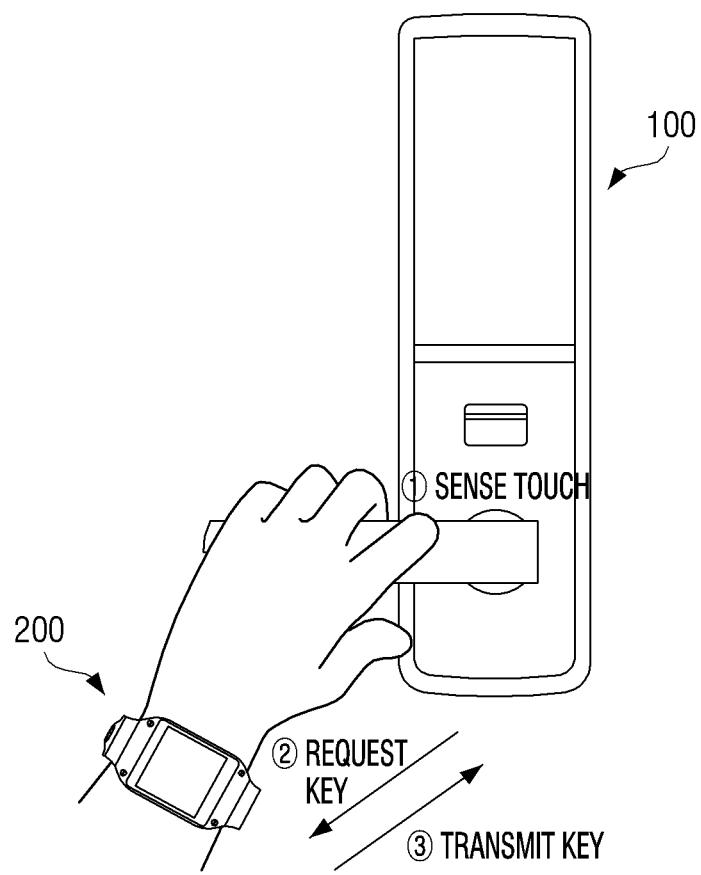
FIGS. 7A and 7B are views for describing key information transmission methods according to various embodiments of the present disclosure.

FIG. 7A is a view for describing signal transmission start of a user terminal apparatus 200 according to an embodiment of the present disclosure.

Referring to FIG. 7A, the electronic apparatus 100 may further include a sensor sensing a touch with the human body, and when the touch with the human body is sensed by the sensor (I), the processor 130 of the electronic apparatus 100 controls the communication interface 120 to transmit the key information request signal through the touched human body (D). The key information request signal may include at least one of information on a type of the electronic apparatus 100 and unique information of the electronic apparatus 100. A plurality of key information corresponding to each of a plurality of apparatuses including the electronic apparatus 100 may be stored in the user terminal apparatus 200, and the user terminal apparatus 200 may transmit a signal including the key information corresponding to the information on the type of the electronic apparatus 100 and/or the unique information of the electronic apparatus 100 among the plurality of key information to the electronic apparatus 100 through the user's body (a) when it receives the key information request signal through the user's body. When the signal is received through the touched human body, the processor 130 of the electronic apparatus 100 obtains the key information from the received signal.

As another example, the user terminal apparatus 200 may trigger the transmission of the signal. The user terminal apparatus 200 worn on a user's arm may sense motion, a change in an electrical potential of a muscle, and the like, using, for example, a motion sensor, an electromyogram sensor, and the like, to recognize situations such as a case in which the user holds a door of the electronic apparatus 100, a case in which the user pulls a knob of the door, and a case in which the user turns the knob of the door, and the like. The user terminal apparatus 200 may transmit the signal including the key information to the electronic apparatus 100 through the human body communication when these situations are recognized. The present embodiment will be described with reference to FIG. 7B.

Figure 7B:
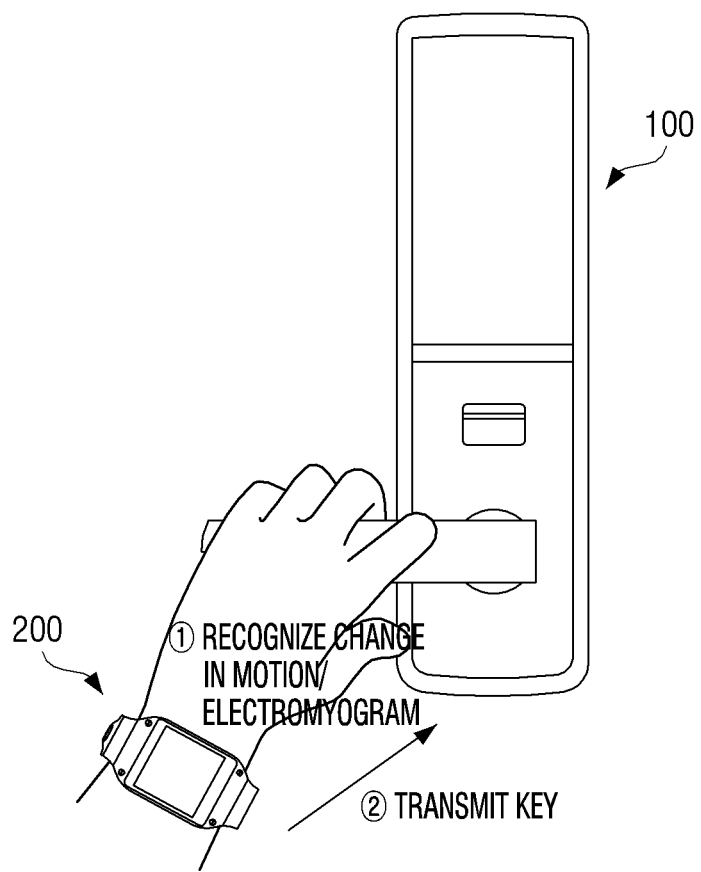

FIG. 7B is a view for describing signal transmission start of a user terminal apparatus 200 according to an embodiment of the present disclosure.

Referring to FIG. 7B, the user terminal apparatus 200 worn on a user's wrist may confirm what the user holds and turns by sensing a change in a motion and/or a change in electromyogram depending on movement of a muscle.

When it is sensed what the user holds and turns (①), the user terminal apparatus 200 controls the communication interface 120 to transmit the signal including the key information through the human body. When the signal is received through the human body, the processor 130 of the electronic apparatus 100 obtains the key information from the received signal.

The electronic apparatus 100 obtains the key information from the signal received from the user terminal apparatus 200, and confirms whether or not the key information corresponds to the authentication key information corresponding to the predetermined function at operation S650. When the key information does not correspond to the authentication key information as a confirmation result (S650: N), the electronic apparatus 100 decides that authentication fails at operation S670. When the key information corresponds to the authentication key information as a confirmation result (S650: Y), the electronic apparatus 100 confirms whether or not the waveform of the received signal corresponds to the stored waveform information at operation S660. When the waveform of the received signal does not correspond to the stored waveform information as a confirmation result (S660: N), the electronic apparatus 100 decides that authentication fails at operation S670. When the waveform of the received signal corresponds to the stored waveform information as a confirmation result (S660: Y), the electronic apparatus 100 performs the predetermined function corresponding to the authentication key information at operation S690.

When it is decided that the authentication fails at operation S670, the electronic apparatus 100 may notify the user terminal apparatus 200 of the failure of the authentication at operation S680. In this case, the electronic apparatus 100 may transmit information for notifying the user terminal apparatus 200 of the failure of the authentication to the user terminal apparatus 200 through the human body communication or transmit the information in other communication manners. The user terminal apparatus 200 receiving the notification for the failure of the authentication may display a phrase such as "authentication fails", "please attempt again", or the like, on, for example, a display of the user terminal apparatus 200 to notify the user of the failure of the authentication at operation S680. Meanwhile, the notification for the failure of the authentication may be performed by the user terminal apparatus 200 as described above or be performed by the electronic apparatus 100. For example, the electronic apparatus 100 may output a predetermined authentication failure notifying sound through a speaker of the electronic apparatus 100 or may display the phrase such as "authentication fails", "please attempt again", or the like, through the display of the electronic apparatus 100. In the case in which the notification for the failure of the authentication is performed by the electronic apparatus 100 as described above, S680 may be omitted.

Meanwhile, the predetermined function performed at operation S690 may be various depending on use purposes of the electronic apparatus 100. As an example, in the case in which the electronic apparatus 100 is a front door lock apparatus, the predetermined function may be a function of releasing a locking state of a front door. For example, in the case in which the electronic apparatus 100 is a door lock apparatus of a car, the predetermined function may be a function of releasing a locking state of a door of the car. As another example, in the case in which the electronic apparatus 100 is a desktop computer, a tablet PC, a smartphone, or the like, the predetermined function may be a function of releasing a locking state (for example, a function of switching a locking screen into a home screen) so that the desktop computer, the tablet PC, the smartphone, or the like, may be used. As still another example, in the case in which the electronic apparatus 100 is a car, the predetermined function may be a function of releasing a locking state of a door of the car and changing (for example, changing a driver's seat gradient, a room mirror angle, a rearview mirror angle, and the like) car setting depending on setting information prestored in the storage 110 according to the waveform information.

Meanwhile, when the user terminal apparatus 200 continues to transmit the signal including the key information even after the authentication succeeds, a battery of the user terminal apparatus 200 may be unnecessarily consumed. Therefore, according to an embodiment of the present disclosure, when the authentication succeeds, the electronic apparatus 100 may transmit information for notifying the user terminal apparatus 200 of the success of the authentication to the user terminal apparatus 200. This will be described with reference to FIG. 8A.

Figure 8A:
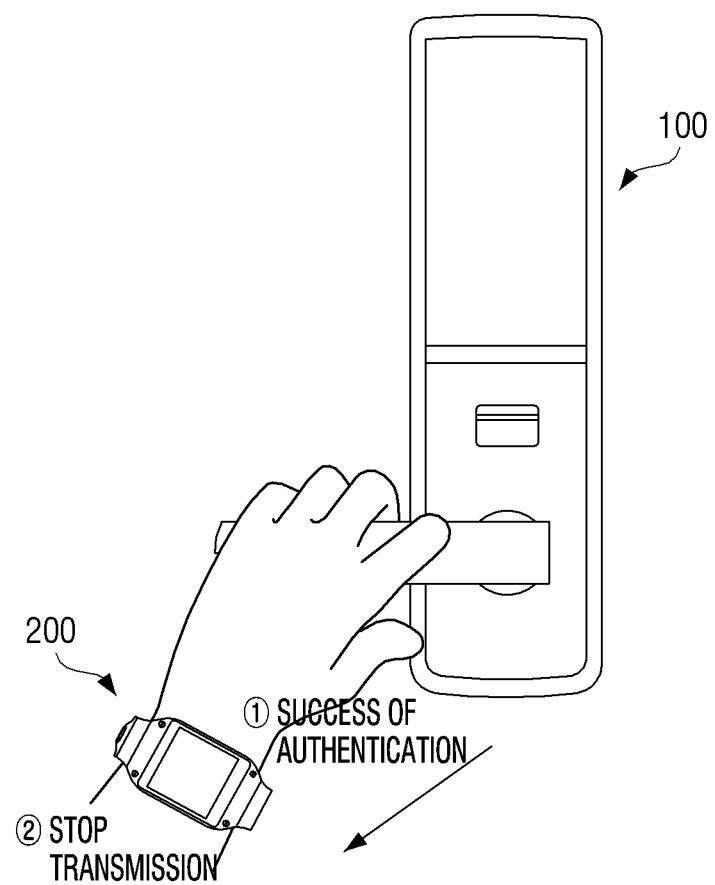
FIGS. 8A and 8B are views for describing key information transmission stopping methods according to various embodiments of the present disclosure.
Figure 8B:
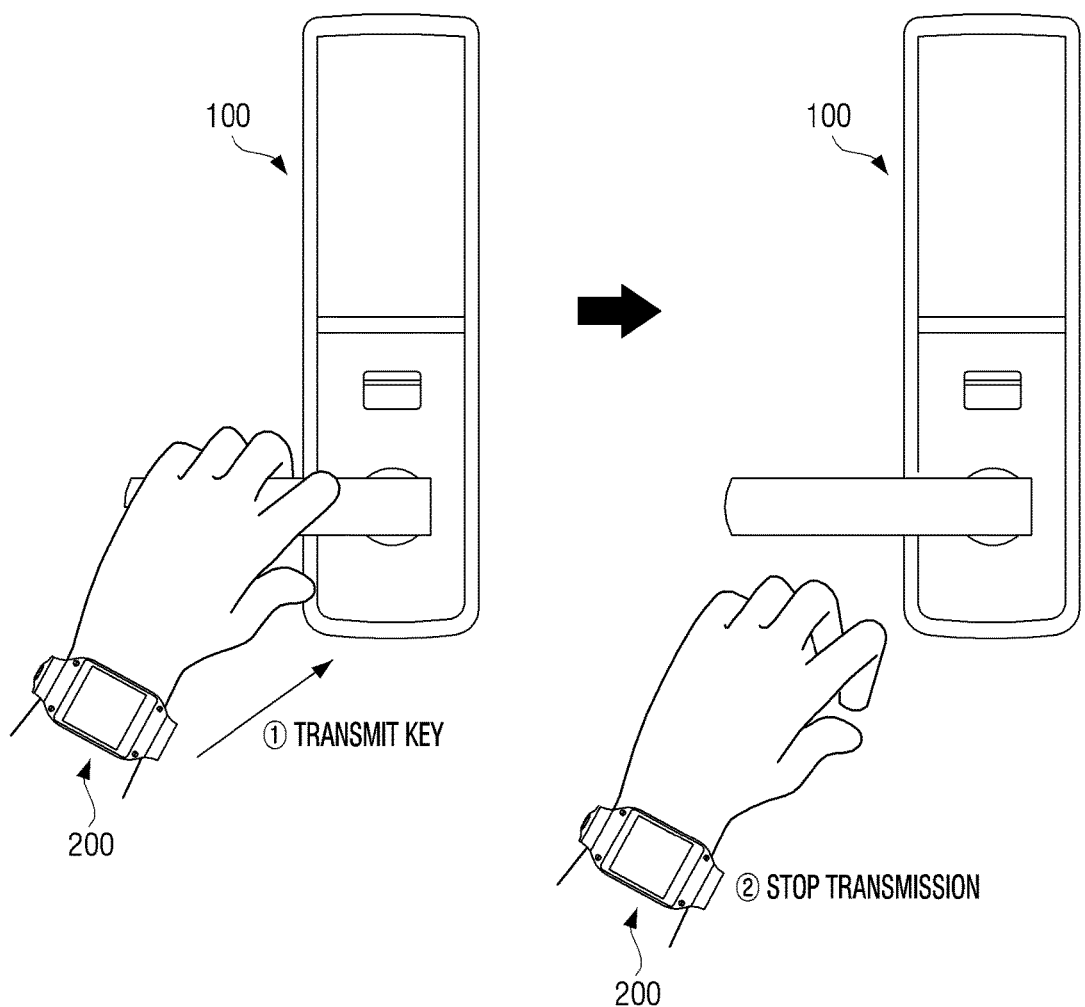

FIGS. 8A and 8B are views for describing key information transmission stopping methods according to various embodiments of the present disclosure.

Referring to FIG. 8A, when the key information corresponds to the authentication key information in S650 and the waveform of the signal corresponds to the stored waveform information in S660, the electronic apparatus 100 may transmit a signal including the information for notifying the user terminal apparatus 200 of the success of the authentication to the user terminal apparatus 200 through the user's body (①). The user terminal apparatus 200 receiving the signal stops transmitting the signal including the key information (②). In this case, for example, a phrase "authentication succeeds" may be displayed on the display of the user terminal apparatus 200.

Meanwhile, stopping transmitting the signal including the key information may be performed by the user terminal apparatus 200 itself. The present embodiment will be described with reference to FIG. 8B.

Referring to FIG. 8B, the user terminal apparatus 200 transmits the signal including the key information (①), and may stop transmitting the signal including the key information (②) when it is confirmed that the user holding something does not hold something any more through a change in a motion, a change in electromyogram, or the like.

According to another embodiment, the user terminal apparatus 200 may sense a change in a potential between an electrode for human body communication provided in the electronic apparatus 100 and an electrode provided in the user terminal apparatus 200 to confirm whether or not the user wearing the user terminal apparatus 200 touches the electronic apparatus 100, and may transmit the signal including the key information to the electronic apparatus 100 through the human body when the user touches the electronic apparatus 100 as a confirmation result and may not transmit the signal including the key information to the electronic apparatus 100 when the user does not touch the electronic apparatus 100 as a confirmation result.

Meanwhile, in the case in which the user terminal apparatus 200 needs to transmit the signal including the key information to the electronic apparatus 100, the user terminal apparatus 200 may transmit the signal including the key information to the electronic apparatus 100 after it verifies whether or not the user wearing the user terminal apparatus 200 is a valid user of the user terminal apparatus 200. Therefore, security may be further enhanced.

In detail, in the case in which the user terminal apparatus 200 needs to transmit the signal including the key information to the electronic apparatus 100, the user terminal apparatus 200 may compare physical feature information collected up to now and physical feature information of a person currently wearing the user terminal apparatus 200 with each other to confirm whether or not the person currently wearing the user terminal apparatus 200 is the valid user of the user terminal apparatus 200. The user terminal apparatus 200 may transmit the signal including the key information to the electronic apparatus 100 under the condition that the confirmation is conducted. Therefore, even though a thief stealing the user terminal apparatus 200 wears the user terminal apparatus 200 and holds the electronic apparatus 100, the signal including the key information is not transferred to the electronic apparatus 100.

Meanwhile, in the case in which the confirmation function of the user terminal apparatus 200 as described above is lost by a cracker, even though the thief wears the user terminal apparatus 200 and holds the electronic apparatus 100, the signal including the key information may be transmitted to the electronic apparatus 100. However, in the present disclosure, the electronic apparatus 100 may decide from which user the signal is transmitted on the basis of the waveform information, and security may thus be ensured even in this case. This will be described in more detail with reference to FIG. 9.

FIG. 9 is a view for describing a user authentication method of an electronic apparatus according to an embodiment of the present disclosure.

Referring to FIG. 9, when a valid user 10 of the user terminal apparatus 200 and the electronic apparatus 100 wears the user terminal apparatus 200 and touches the electronic apparatus 100, the user terminal apparatus 200 transmits a signal including A key information to the electronic apparatus 100 (①). The electronic apparatus 100 obtains the A key information from the received signal, compares the A key information with pre-stored authentication key information, and releases a locking state of a door of a car (②) when it is confirmed that the A key information coincides with pre-stored authentication key information and it is confirmed that a waveform of the received signal corresponds to pre-stored waveform information of the valid user 10.

However, a situation in which the user terminal apparatus 200 is stolen by a thief 20 (e.g., an unauthorized user) may occur. In this case, when the thief 20 wearing the user terminal apparatus 200 touches the electronic apparatus 100, a signal including A key information may be transmitted from the user terminal apparatus 200 to the electronic apparatus 100 (①). However, since physical components of the valid user 10 and physical components of the thief 20 are different from each other, even though the signal received through a body of the valid user 10 and the signal received through a body of the thief 20 have the same A key information, waveforms of these signals are different from each other. Therefore, even though the A key information obtained from the signal received from the thief 20 coincides with the pre-stored authentication key information, the electronic apparatus 100 does not open the door (②) since the waveform of the received signal does not coincide with the pre-stored waveform information of the valid user 10. The physical components of a user are unique to that user, and may be influenced in part by various factors, including for example, the user's weight, height, volume, density, fluid level, bone mass, relative fat content, relative muscle content, etc.

According to an embodiment of the present disclosure, when the thief 20 attempts to open the door of the car, the electronic apparatus 100 may not only allow the door of the car not to be opened, but also perform a burglar alarm function. In other words, when the communication interface 120 of the electronic apparatus 100 receives the signal through the human body, the processor 130 of the electronic apparatus 100 may obtain the key information from the received signal, and perform the burglar alarm function when the obtained key information corresponds to the pre-stored authentication key information, but the waveform of the received signal does not correspond to the pre-stored waveform information.

As an example, the burglar alarm function of the electronic apparatus 100 may be a function of transmitting a control command for allowing the user terminal apparatus 200 to be operated in a stolen state to the user terminal apparatus 200. The user terminal apparatus 200 receiving the control command is switched into a locking state so that the thief 20 may not use the user terminal apparatus 200, and may transmit information for notifying the valid user 10 that the user terminal apparatus 200 is stolen and/or information on a current position of the user terminal apparatus 200 to another user terminal apparatus (for example, a smal (phone) of the valid user 10 interlocked with the user terminal apparatus 200. As another example, the burglar alarm function of the electronic apparatus 100 may be a function of sounding a horn of the car. As still another example, the burglar alarm function of the electronic apparatus 100 may be a function of transmitting information for notifying the valid user 10 that the user terminal apparatus 200 is stolen and/or information on a current position of the electronic apparatus 100 to another user terminal apparatus (for example, a smal (phone) of the valid user 10.

Meanwhile, when physical components of the user are changed (for example, when the user exercises hard, such that fat of the user is decreased and a muscle of the user is increased), the waveform of the signal may be changed. Therefore, according to an embodiment of the present disclosure, the waveform information may be periodically updated.

For example, when the waveform of the signal that the communication interface 120 of the electronic apparatus 100 receives through the human body corresponds the stored waveform information, that is, similarity between the waveform of the received signal and the waveform information of the stored signal is in a predetermined error range, the processor 130 of the electronic apparatus 100 may generate waveform information on the basis of the waveform of the received signal, and update the waveform information pre-stored in the storage 110 on the basis of the generated waveform information. The update may include an operation of replacing the pre-stored waveform information by the generated waveform information or generating new waveform information in which both of the generated waveform information and the pre-stored waveform information are reflected and storing the new waveform information in the storage 110.

The electronic apparatus 100 may include a plurality of electrodes for receiving the signal through the human body communication, and the electrodes may be, for example, disposed on each of a knob of the door of the car and a steering wheel of the car. The electronic apparatus 100 may perform a locking state releasing operation through the electrode disposed on the knob of the door of the car, and may receive the signal from the user through the human body communication in the case in which the user holds the steering wheel through the electrode disposed on the steering wheel and update the pre-stored waveform information with respect to the user on the basis of the received signal.

According to the various embodiments described above, the user may easily release the locking state of the electronic apparatus through the human body communication, and the security may be more certainly ensured through double verification including a digital verification process based on the key information obtained from the signal and an analog verification process based on the waveform of the signal.

Figure 10:
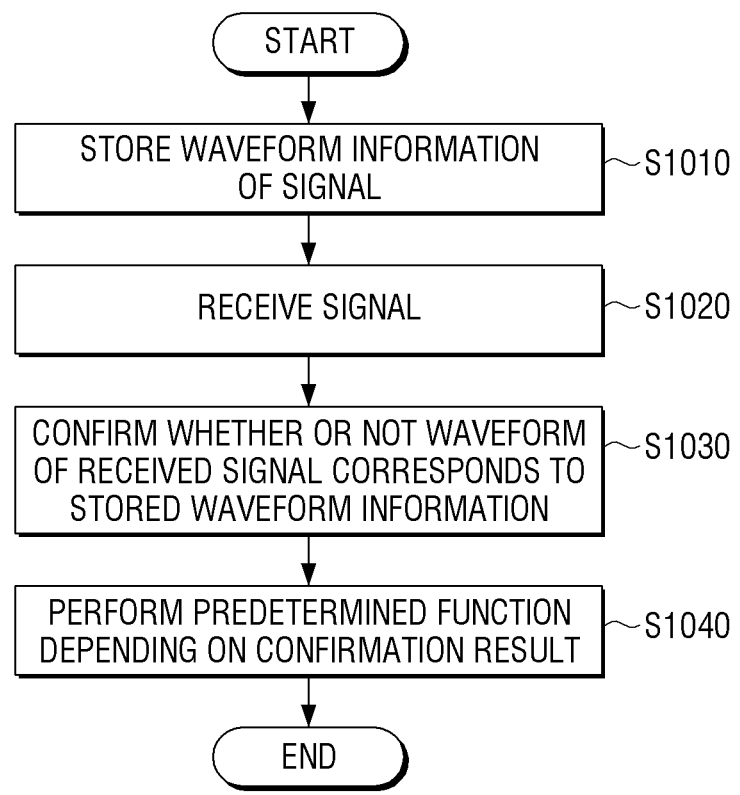
FIG. 10 is a view for describing a controlling method of an electronic apparatus according to an embodiment of the present disclosure.

FIG. 10 is a flow chart for describing a controlling method of an electronic apparatus according to an embodiment of the present disclosure.

Referring to FIG. 10, the electronic apparatus stores the waveform information of the signal received from the user's body at operation S1010. For example, in the case in which the electronic apparatus is the car, the electrode is provided on the steering wheel, and when the user holds the steering wheel, the electronic apparatus receives the signal from the user's body through the electrode and stores the waveform information of the received signal. The waveform information of the signal may be periodically collected and updated. The waveform information, which indicates electrical characteristics of the signal, may indicate a potential, a distortion level, noise, or the like, of the signal.

In addition, the electronic apparatus may obtain the key information from the signal received from the user terminal apparatus, and store the obtained key information as the authentication key information related to the predetermined function. The key information may be the physical feature information (for example, a fingerprint, ECG, a gait pattern, and the like) of the user generated from the user terminal apparatus worn by the user. The electronic apparatus may periodically receive the key information transferred from the user terminal apparatus to update the authentication key information.

Then, the electronic apparatus receives the signal from the external apparatus using the human body as a communication medium at operation S1020. For example, the signal is received through the steering wheel at operation S1010, while the signal may be received through the knob of the car at operation S1020. In addition, the electronic apparatus confirms whether or not the waveform of the received signal corresponds to the stored waveform information at operation S1030. That is, the electronic apparatus confirms whether or not the waveform of the signal received in S1020 corresponds to the waveform information stored at operation S1010.

In addition, the electronic apparatus may obtain the key information from the signal received at operation S1020, and confirm whether or not the obtained key information corresponds to the pre-stored authentication key information.

The electronic apparatus performs the predetermined function at operation S1040 depending on a confirmation result at operation S1030.

For example, in the case in which the potential, the distortion level, the noise, or the like, of the signal received in S1020 does not correspond to a potential, a distortion level, noise, or the like, included in the waveform information stored in S1010, the electronic apparatus does not perform the predetermined function.

When the key information obtained from the signal received from the user terminal apparatus through the human body corresponds to the pre-stored authentication key information and the waveform of the received signal does not correspond to the pre-stored waveform information, the electronic apparatus may transmit information for notifying the user terminal apparatus that the predetermined function may not be executed to the user terminal apparatus. Alternatively, in this case, the electronic apparatus may perform the burglar alarm function.

Figure 11:
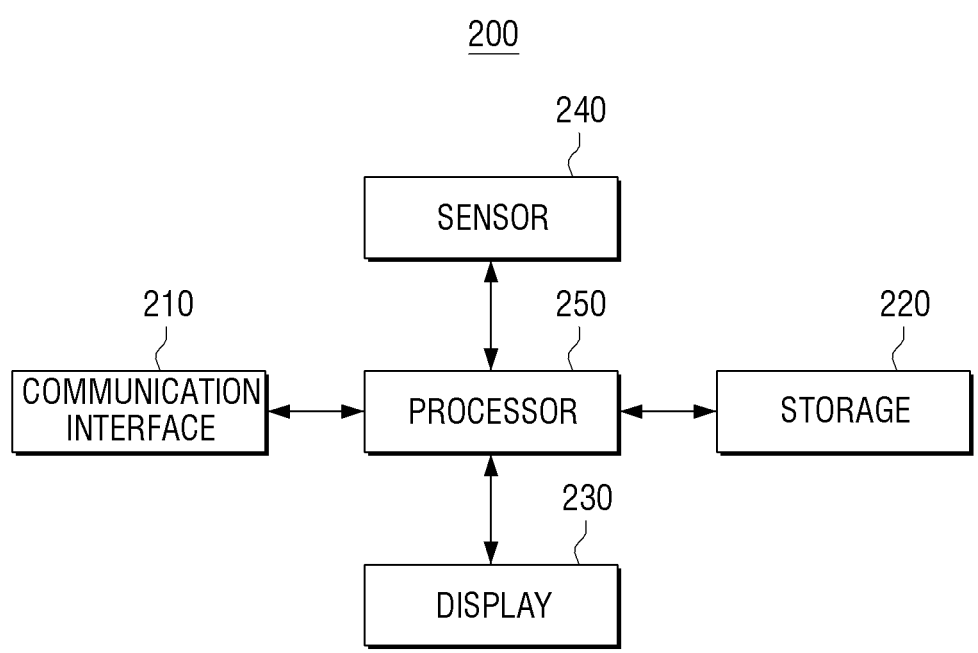
FIG. 11 is a block diagram for describing components of a user terminal apparatus according to an embodiment of the present disclosure.

FIG. 11 is a block diagram for describing components of a user terminal apparatus 200 according to an embodiment of the present disclosure.

Referring to FIG. 11, the user terminal apparatus 200 may include a communication interface 210 (e.g., a transceiver), a storage 220 (e.g., a memory), a display 230, a sensor 240 (e.g., at least one sensor), and a processor 250 (e.g., at least one processor).

The communication interface 210 is a component for performing communication with various external apparatuses. The communication interface 210 may perform communication in various communication manners. As an example, the communication interface 210 may perform communication with an external apparatus in a human body communication manner, which is a manner of transmitting and receiving signals using a human body as a communication medium. In this case, the communication interface 210 includes an electrode touching the human body to receive a signal. The electrode may direct touch the human body or touch the human body with a coating, or the like, interposed therebetween. The communication medium, including a user connected thereto, may function as an antenna of the communication interface 210.

As another example, the communication interface 210 may be connected to the external apparatus through an LAN or an Internet network, and may be connected to the external apparatus in a wireless communication manner (for example, Z-wave, 4LoWPAN, 6LoWPAN, RFID, LTE D2D, BLE, GPRS, Weightless, Edge Zigbee, ANT+, NFC, IrDA, DECT, WLAN, Bluetooth, WiFi, WiFi direct, GSM, UMTS, LTE, WiBRO, or the like). The communication interface 210 may include various communication chips such as a WiFi chip, a Bluetooth chip, a wireless communication chip, and the like.

Meanwhile, the storage 220 may be implemented by a non-volatile memory, a volatile memory, a flash memory, a hard disc drive (HDD), a solid-state drive (SSD), or the like. The storage 220 is accessed by the processor 250, and readout, recording, correction, deletion, update, and the like, of data in the storage 220 may be performed by the processor 250. Meanwhile, the storage 220 may be implemented by an external storage medium, for example, a universal serial bus (USB), a web server through a network, or the like, as well as a storage medium in the user terminal apparatus 200.

An operating system (O/S) or programs such as various applications and various data such as user set data may be stored in the storage 220.

The storage 220 may store physical feature information of the user collected from the user at ordinary times. The used physical feature information may be used to authenticate the user.

The storage 220 may store key information for each of a plurality of electronic apparatuses including the electronic apparatus 100. Alternatively, the storage 220 may store key information for each of types of the plurality of electronic apparatuses. The stored key information may be used to release locking of the electronic apparatus.

The display 230 is a component for displaying various screens. The display 230 may be implemented by, for example, a liquid crystal display (LCD), and may be implemented by a cathode-ray tube (CRT), a plasma display panel (PDP), an organic light emitting diode (OLED), a transparent OLED (TOLED), or the like, in some cases. In addition, the display 230 may be also be implemented in a form of a touch screen that may sense a touch manipulation of the user.

The sensor 240 may be implemented by various sensors such as a motion sensor (for example, an acceleration sensor, a gyro sensor, a gravity sensor, or the like), an electromyogram change sensor, an electrocardiogram sensor, and the like.

The processor 250 is a component for controlling a general operation of the user terminal apparatus 200. The processor 250 may be implemented by, for example, a CPU, an ASIC, or the like.

The user terminal apparatus 200 may be a wearable device, and the processor 250 may collect the physical feature information of the user during a period in which the user wears the user terminal apparatus 200 through the sensor 240, or the like. The physical feature information collected as described above may be compared with physical feature information collected from a user currently wearing the user terminal apparatus 200 to be used to decide whether or the user currently wearing the user terminal apparatus 200 is a valid user.

In addition, the processor 250 may generate key information on the basis of the physical feature information. In addition, the processor 250 may transmit the key information to the electronic apparatus 100 to register the key information as authentication key information. As described above, the key information generated on the basis of the physical feature information may be transmitted to the electronic apparatus 100 without transmitting the physical feature information to the electronic apparatus 100 as it is, thereby preventing a risk that the physical feature information, which is personal information, will be leaked to the outside.

In addition, the processor 250 may transmit the key information to the electronic apparatus 100 when a locking state of the electronic apparatus 100 needs to be released, and the electronic apparatus 100 may confirm whether or not the received key information corresponds to registered authentication key information and then release the locking state.

The electronic apparatus 100 may transmit at least one of unique information (for example, an ID code) of the electronic apparatus and information (for example, information on whether the electronic apparatus is a car or a front door) on a type of the electronic apparatus to the user terminal apparatus 200, and the processor 250 may transmit key information corresponding to the unique information of the electronic apparatus 100 or the type of the electronic apparatus 100 among a plurality of key information stored in the storage 110 to the electronic apparatus 100.

The processor 250 may decide whether or not the key information needs to be transmitted on the basis of a change in electromyogram or a change in a motion of the user wearing the user terminal apparatus 200, sensed by the sensor 240. Alternatively, the processor 250 may transmit the key information to the electronic apparatus 100 depending on the key information request signal received from the electronic apparatus 100.

In addition, the processor 250 may stop transmitting the key information on the basis of a change in electromyogram or a change in a motion of the user wearing the user terminal apparatus 200, sensed by the sensor 240. Alternatively, the processor 250 may stop transmitting the key information on the basis of the authentication completion signal received from the electronic apparatus 100.

The processor 250 may control the display 230 to display various UIs. For example, the processor 250 may control the display 230 to display the UI for key registration described with reference to FIGS. 4A and 4B. In addition, the processor 250 may display information on whether or not the authentication succeeds in the electronic apparatus 100 after the transmission of the key information through the display 230.

Figure 12:
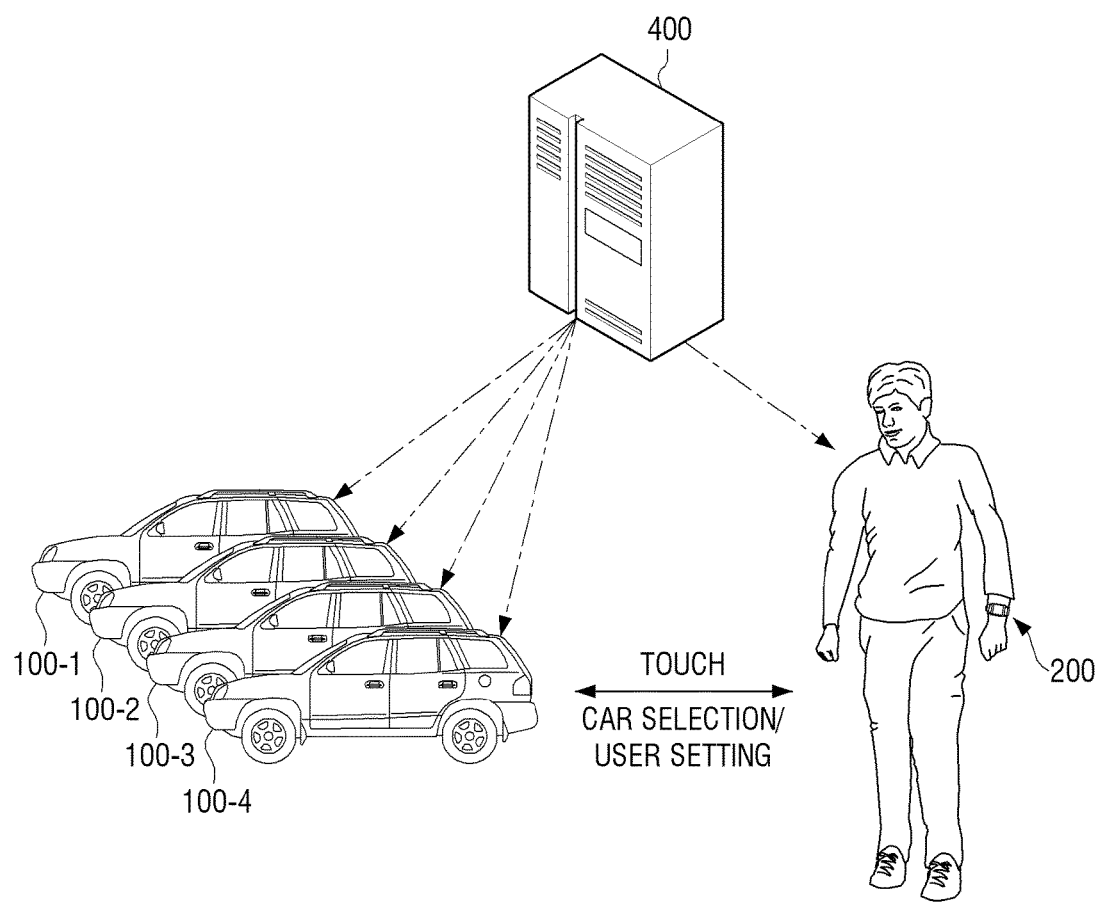
FIG. 12 is a view for describing a car sharing system according to an embodiment of the present disclosure.

FIG. 12 is a view for describing a car sharing system according to an embodiment of the present disclosure.

Referring to FIG. 12, a user may use a car only by touching a desired car of a plurality of sharing cars 100-1, 100-2, 100-3, and 100-4.

In detail, when the user conducts a use contract with a car sharing company and payment, a managing server 400 of the car sharing company transmits car use key information to a user terminal apparatus 200. In addition, the managing server 400 transmits the same car use key information to the plurality of sharing cars 100-1 to 100-4.

When the user touches the desired car of the plurality of sharing cars 100-1 to 100-4, the user terminal apparatus 200 may transmit the car use key information provided from the managing server 400 to the selected car through human body communication, the selected car may confirm whether or not the car use key information received from the user terminal apparatus 200 coincides with car use key information that the selected car receives in advance from the managing server 400, and a locking state of a door of the selected car may be released when it is confirmed that the car use key information received from the user terminal apparatus 200 coincides with the car use key information that the selected car receives in advance from the managing server 400. According to another embodiment, the plurality of sharing cars 100-1 to 100-4 may transmit car use key information to the managing server 400 when the car use key information is transmitted from the user terminal apparatus 200 and then confirm whether or not the car use key information is appropriate car use key information, instead of receiving the car use key information in advance from the managing server 400.

In addition, the user terminal apparatus 200 may transmit information for car setting (for example, a seat gradient, address information of favorite places, and the like) to the selected car through the human body communication. The car receiving the information for car setting may perform an operation of adjusting the seat gradient, an operation of registering addresses of the favorite places in a navigation device, and the like, depending on the received information.

Figure 13:
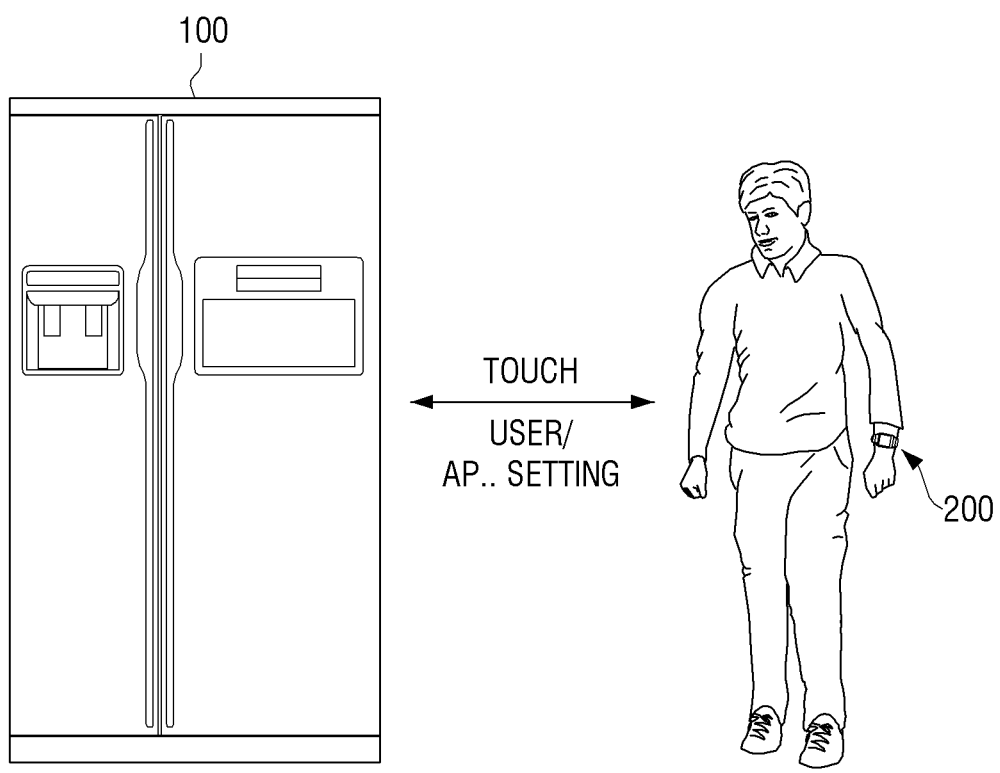
FIG. 13 is a view for describing a device setting method according to an embodiment of the present disclosure.

FIG. 13 is a view for describing a product initial setting method according to an embodiment of the present disclosure.

FIG. 13 illustrates a case in which the electronic apparatus 100 is implemented by a refrigerator. Even though the user only touches the electronic apparatus 100, the user terminal apparatus 200 may transmit various setting information to the electronic apparatus 100 through the human body communication to allow the electronic apparatus 100 to be set. For example, the user terminal apparatus 200 may transmit AP information, connection device information, and the like, to the electronic apparatus 100 through the human body communication, and the electronic apparatus 100 may perform network setting on the basis of the received information.

According to the present embodiment, initial setting of a newly purchased device may be readily conducted only by touching the newly purchased device without needing to perform a complicated manipulation.

Meanwhile, the diverse embodiments of the present disclosure described above may be implemented in a computer or a computer readable recording medium using software, hardware, or a combination of software and hardware. As an example, according to a hardware implementation, various embodiments described in the present disclosure may be implemented using at least one of application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, and electric units for performing other functions. According to a software implementation, various embodiments such as procedures and functions described in the present disclosure may be implemented by separate software modules. Each of the software modules may perform one or more functions and operations described in the present disclosure.

Meanwhile, the controlling methods of an electronic apparatus or the controlling method of a user terminal apparatus according to the various embodiments of the present disclosure described above may be stored in a non-transitory readable medium. The non-transitory readable medium may be mounted and used in various apparatuses.

The non-transitory computer readable medium is not a medium that stores data therein for a while, such as a register, a cache, a memory, or the like, but means a medium that semi-permanently stores data therein and is readable by a device. In detail, programs for performing the diverse methods described above may be stored and provided in the non-transitory computer readable medium such as a compact disc (CD), a digital versatile disc (DVD), a hard disc, a Blu-ray disc, a universal serial bus (USB), a memory card, a read only memory (ROM), or the like.

According to an embodiment, the methods according to the various embodiments disclosed in the present document may be included and provided in a computer program product. The computer program product may be traded as a product between a seller and a purchaser. The computer program product may be distributed in a form of a storage medium (for example, a compact disc read only memory (CD-ROM)) that may be read by a device or online through an application store (for example, PlayStore™). In the case of the online distribution, at least portions of the computer program product may be at least temporarily stored in a storage medium such as a memory of a server of a manufacturer, a server of an application store, or a relay server or be temporarily generated.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. An electronic apparatus comprising:
a memory for storing waveform information corresponding to a user and authentication key information corresponding to a function;
a transceiver configured to be coupled to an external electronic apparatus through a human body; and
at least one processor configured to:
receive a signal carrying key information from the external electronic apparatus through the user's body by using the transceiver, wherein the signal is generated by the external electronic apparatus,
confirm whether or not a waveform of the received signal corresponds to the stored waveform information and whether or not the key information corresponds to the stored authentication key information, wherein the waveform of the received signal is different according to transfer paths of the signals, and
perform the function depending on the confirmation result.

2. The electronic apparatus as claimed in claim 1, wherein the at least one processor is further configured to control the transceiver to transmit information for notifying the external electronic apparatus that execution of the function is impossible to the external electronic apparatus when the key information corresponds to the stored authentication key information and the waveform of the received signal does not correspond to the stored waveform information.

3. The electronic apparatus as claimed in claim 1, wherein the at least one processor is further configured to perform a burglar alarm function when the key information corresponds to the stored authentication key information and the waveform of the received signal does not correspond to the stored waveform information.

4. The electronic apparatus as claimed in claim 1, wherein the at least one processor is further configured to store waveform information generated on the basis of a waveform of a key registration signal in the memory and stores key information obtained from the key registration signal as the authentication key information corresponding to the function in the memory, when the transceiver receives the key registration signal through the user's body.

5. The electronic apparatus as claimed in claim 1, further comprising:
a sensor configured to sense a touch with the user's body,
wherein the at least one processor is further configured to control the transceiver to:
transmit a key information request signal through the touched user's body when the touch with the user's body is sensed by the sensor, and
obtain the key information from a signal when the signal is received from the touched user's body.

6. The electronic apparatus as claimed in claim 5, wherein the key information request signal includes at least one of information on a type of the electronic apparatus or unique information of the electronic apparatus.

7. The electronic apparatus as claimed in claim 1, wherein the at least one processor is further configured to, when the waveform of the received signal corresponds to the stored waveform information:
generate waveform information on the basis of the waveform of the received signal, and
update the stored waveform information on the basis of the generated waveform information.

8. The electronic apparatus as claimed in claim 1,
wherein the electronic apparatus comprises an electronic lock apparatus, and
wherein the function is a function of releasing a locking state of the electronic lock apparatus.

9. A controlling method of an electronic apparatus, the controlling method comprising:
storing waveform information of a signal corresponding to a user and authentication key information corresponding to a function;
receiving a signal carrying key information from an external electronic apparatus through a user's body, wherein the signal is generated by the external electronic apparatus;

confirming whether or not a waveform of the received signal corresponds to the stored waveform information and confirming whether or not the key information corresponds to the stored authentication key information, wherein the waveform of the received signal is different according to transfer paths of the signals; and performing the function depending on the confirmation result.

10. The controlling method of an electronic apparatus as claimed in claim 9, further comprising:

transmitting information for notifying the external apparatus that execution of the function is impossible to the external apparatus when the key information corresponds to the stored authentication key information and the waveform of the received signal does not correspond to the stored waveform information.

11. The controlling method of an electronic apparatus as claimed in claim 9, further comprising:

performing a burglar alarm function when the key information corresponds to the stored authentication key information and the waveform of the received signal does not correspond to the stored waveform information.

12. The controlling method of an electronic apparatus as claimed in claim 9, further comprising:

receiving a key registration signal from the external electronic apparatus using the user's body as a communication medium, wherein the storing of the waveform information includes storing waveform information generated on the basis of a waveform of the received key registration signal, and wherein the storing of the authentication key information includes storing key information obtained from the received key registration signal as the authentication key information corresponding to the function.

13. The controlling method of an electronic apparatus as claimed in claim 9, further comprising:

transmitting a key information request signal through a touched user's body when a touch with the user's body is sensed, wherein in the receiving of the key information, the key information is obtained from a signal when the signal is received through the touched user's body.

14. The controlling method of an electronic apparatus as claimed in claim 13, wherein the key information request signal includes at least one of information on a type of the electronic apparatus or unique information of the electronic apparatus.

15. The controlling method of an electronic apparatus as claimed in claim 9, further comprising:

generating waveform information on the basis of the waveform of the received signal, and updating the stored waveform information on the basis of the generated waveform information, when the waveform of the received signal corresponds to the stored waveform information.

16. The controlling method of an electronic apparatus as claimed in claim 9, wherein the electronic apparatus comprises an electronic lock apparatus, and wherein the function comprises a function of releasing a locking state of the electronic lock apparatus.

17. The controlling method of an electronic apparatus as claimed in claim 9, wherein the communication medium functions as an antenna.

18. A non-transitory computer-readable recording medium having an executable program recorded thereon, wherein the program instructs a computer to perform:

storing waveform information of a signal corresponding to a user and authentication key information corresponding to a function;

receiving a signal carrying key information from an external electronic apparatus using a user's body, wherein the signal is generated by the external electronic apparatus;

confirming whether or not a waveform of the received signal corresponds to the stored waveform information and confirming whether or not the key information corresponds to the stored authentication key information, wherein the waveform of the received signal is different according to transfer paths of the signals; and performing the function depending on the confirmation result.

* * * * *